(12) United States Patent
Uhrich et al.

(10) Patent No.: US 9,387,250 B2
(45) Date of Patent: Jul. 12, 2016

(54) THERAPEUTIC COMPOSITIONS FOR BONE REPAIR

(71) Applicants: Rutgers, the State University of New Jersey, New Brunswick, NJ (US); The Trustees of the University of Pennsylvania, Philadelphia, PA (US)

(72) Inventors: Kathryn E. Uhrich, New Brunswick, NJ (US); Dana Graves, Philadelphia, PA (US); Keisuke Wada, Philadelphia, PA (US); Joseph P. Fiorellini, Philadelphia, PA (US); Michelle Morano, New Brunswick, NJ (US); Roselin Rosario-Meléndez, New Brunswick, NJ (US); Sabrina Sachiko Snyder, New Brunswick, NJ (US)

(73) Assignees: Rutgers, The State University of New Jersey, New Brunswick, NJ (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/218,492

(22) Filed: Mar. 18, 2014

(65) Prior Publication Data
US 2014/0271864 A1 Sep. 18, 2014

Related U.S. Application Data

(60) Provisional application No. 61/793,507, filed on Mar. 15, 2013.

(51) Int. Cl.
*A61P 19/08* (2006.01)
*A61K 31/60* (2006.01)
*A61K 31/192* (2006.01)
*A61K 45/06* (2006.01)
*A61L 27/58* (2006.01)
*A61K 33/00* (2006.01)
*A61L 29/16* (2006.01)
*A61K 47/48* (2006.01)

(52) U.S. Cl.
CPC .............. *A61K 45/06* (2013.01); *A61K 31/192* (2013.01); *A61K 33/00* (2013.01); *A61K 47/48038* (2013.01); *A61L 27/58* (2013.01); *A61L 29/16* (2013.01)

(58) Field of Classification Search
CPC ...... A61K 33/00; A61K 31/192; A61L 27/58; A61L 29/16
See application file for complete search history.

(56) References Cited

U.S. PATENT DOCUMENTS

| | | |
|---|---|---|
| 2,607,799 A | 8/1952 | Weesner |
| 4,062,855 A | 12/1977 | Allan et al. |
| 4,126,445 A | 11/1978 | Allan et al. |
| 4,164,560 A | 8/1979 | Folkman et al. |
| 4,190,716 A | 2/1980 | Parkinson et al. |
| 4,298,595 A | 11/1981 | Parkinson et al. |
| 4,375,968 A | 3/1983 | Manhart et al. |
| 4,414,203 A | 11/1983 | Cabardo, Jr. et al. |
| 4,559,157 A | 12/1985 | Smith et al. |
| 4,591,496 A | 5/1986 | Cohen et al. |
| 4,608,392 A | 8/1986 | Jacquet et al. |
| 4,612,302 A | 9/1986 | Szabo et al. |
| 4,684,620 A | 8/1987 | Hruby et al. |
| 4,757,128 A | 7/1988 | Domb et al. |
| 4,792,598 A | 12/1988 | Ziegast |
| 4,820,508 A | 4/1989 | Wortzman |
| 4,857,311 A | 8/1989 | Domb et al. |
| 4,868,274 A | 9/1989 | Gupta et al. |
| 4,886,870 A | 12/1989 | D'Amore et al. |
| 4,888,176 A | 12/1989 | Langer et al. |
| 4,891,225 A | 1/1990 | Langer et al. |
| 4,906,474 A | 3/1990 | Langer et al. |
| 4,916,204 A | 4/1990 | Domb et al. |
| 4,938,949 A | 7/1990 | Borch et al. |
| 4,992,478 A | 2/1991 | Geria |
| 4,997,904 A | 3/1991 | Domb |
| 4,999,417 A | 3/1991 | Domb |
| 5,032,216 A | 7/1991 | Felten |
| 5,082,925 A | 1/1992 | Shalaby et al. |

(Continued)

FOREIGN PATENT DOCUMENTS

| | | |
|---|---|---|
| AU | 750424 | 3/2003 |
| CA | 2393676 | 7/2002 |
| DE | 288311 | 3/1991 |
| DE | 0288387 | 3/1991 |
| EP | 0246341 | 11/1987 |
| EP | 0483429 | 5/1992 |
| EP | 0498283 | 8/1992 |
| EP | 0580386 | 1/1994 |
| FR | 2839451 | 11/2003 |

(Continued)

OTHER PUBLICATIONS

American Journal of Pathology. "Diabetes Weakens Your Bones, Research Finds." ScienceDaily. ScienceDaily, Sep. 29, 2009. <www.sciencedaily.com/releases/2009/09/090928095219.htm>. pp. 1-2.*

(Continued)

*Primary Examiner* — Frederick Krass
*Assistant Examiner* — Tracy Liu
(74) *Attorney, Agent, or Firm* — Viksnins Harris & Padys PLLP

(57) ABSTRACT

Individuals having diabetes are more prone to fractures, periodontitis, and other bone related issues as compared to healthy individuals. Furthermore, bone healing in diabetic patients is prolonged. The invention provides a method for decreasing bone resorption or increasing bone formation or promoting bone healing in diabetic patients. In particular, a biodegradable polymer, such as a polyanhydride salicylate is administered at or near a bone defect site, and upon hydrolysis of the polymer will releases biologically active salicylic acid.

17 Claims, 10 Drawing Sheets

(56) References Cited

U.S. PATENT DOCUMENTS

| | | |
|---|---|---|
| 5,160,745 A | 11/1992 | DeLuca et al. |
| 5,175,235 A | 12/1992 | Domb et al. |
| 5,259,968 A | 11/1993 | Emert et al. |
| 5,264,540 A | 11/1993 | Cooper et al. |
| 5,290,494 A | 3/1994 | Coombes et al. |
| 5,317,079 A | 5/1994 | Domb et al. |
| 5,321,113 A | 6/1994 | Cooper et al. |
| 5,364,725 A | 11/1994 | Wilson et al. |
| 5,498,729 A | 3/1996 | Domb |
| 5,512,131 A | 4/1996 | Kumar et al. |
| 5,514,764 A | 5/1996 | Frechet et al. |
| 5,518,730 A | 5/1996 | Fuisz |
| 5,545,409 A | 8/1996 | Laurencin et al. |
| 5,599,552 A | 2/1997 | Dunn et al. |
| 5,610,241 A | 3/1997 | Lee et al. |
| 5,629,009 A | 5/1997 | Laurencin et al. |
| 5,639,468 A | 6/1997 | Rodgers et al. |
| 5,660,851 A | 8/1997 | Domb |
| 5,721,131 A | 2/1998 | Rudolph et al. |
| 5,776,748 A | 7/1998 | Singhvi et al. |
| 5,798,115 A | 8/1998 | Santerre et al. |
| 5,837,278 A | 11/1998 | Geistlich et al. |
| 5,889,028 A | 3/1999 | Sandborn et al. |
| 5,891,477 A | 4/1999 | Lanza et al. |
| 5,902,110 A | 5/1999 | Alfano et al. |
| 5,902,599 A | 5/1999 | Anseth et al. |
| 5,916,585 A | 6/1999 | Cook et al. |
| 5,937,758 A | 8/1999 | Maracas et al. |
| 5,942,252 A | 8/1999 | Tice et al. |
| 5,958,911 A | 9/1999 | Evans et al. |
| 5,969,020 A | 10/1999 | Shalaby et al. |
| 5,990,109 A | 11/1999 | Chen et al. |
| 6,051,255 A | 4/2000 | Conley et al. |
| 6,071,530 A | 6/2000 | Polson et al. |
| 6,123,956 A | 9/2000 | Baker et al. |
| 6,153,212 A | 11/2000 | Mao et al. |
| 6,171,610 B1 | 1/2001 | Vacanti et al. |
| 6,263,880 B1 * | 7/2001 | Parker et al. ............... 128/898 |
| 6,280,772 B1 | 8/2001 | Pinkus |
| 6,365,149 B2 | 4/2002 | Vyakarnam et al. |
| 6,403,675 B1 | 6/2002 | Dang et al. |
| 6,468,519 B1 | 10/2002 | Uhrich |
| 6,486,214 B1 | 11/2002 | Uhrich |
| 6,602,915 B2 | 8/2003 | Uhrich |
| 6,613,807 B2 | 9/2003 | Uhrich |
| 6,685,928 B2 | 2/2004 | Uhrich et al. |
| 6,689,350 B2 | 2/2004 | Uhrich |
| 6,902,578 B1 * | 6/2005 | Anderson et al. ........ 623/16.11 |
| 7,122,615 B1 | 10/2006 | Uhrich |
| 7,396,527 B2 | 7/2008 | Uhrich |
| 7,411,031 B2 | 8/2008 | Uhrich et al. |
| 7,534,852 B2 | 5/2009 | Uhrich |
| 7,662,864 B2 | 2/2010 | Kanamathareddy et al. |
| 7,666,398 B2 | 2/2010 | Uhrich |
| 7,897,599 B2 | 3/2011 | Bowman et al. |
| 7,901,705 B2 | 3/2011 | Roby et al. |
| 7,985,415 B2 | 7/2011 | Giroux |
| 8,017,714 B2 | 9/2011 | Uhrich |
| 8,088,405 B2 * | 1/2012 | Uhrich ...................... 424/426 |
| 8,221,790 B2 | 7/2012 | Uhrich |
| 8,232,322 B2 | 7/2012 | East et al. |
| 8,241,668 B2 | 8/2012 | Uhrich et al. |
| 8,263,060 B2 | 9/2012 | Uhrich et al. |
| 8,361,453 B2 | 1/2013 | Uhrich et al. |
| 8,741,317 B2 | 6/2014 | Uhrich et al. |
| 8,747,832 B2 | 6/2014 | Uhrich et al. |
| 2001/0046476 A1 | 11/2001 | Plochocka |
| 2002/0098161 A1 * | 7/2002 | Uhrich ...................... 424/78.37 |
| 2003/0035787 A1 | 2/2003 | Uhrich et al. |
| 2003/0059469 A1 | 3/2003 | Uhrich et al. |
| 2004/0038948 A1 | 2/2004 | Uhrich et al. |
| 2004/0044125 A1 | 3/2004 | Uhrich et al. |
| 2004/0096476 A1 | 5/2004 | Uhrich et al. |
| 2004/0198641 A1 | 10/2004 | Uhrich et al. |
| 2004/0228832 A1 | 11/2004 | Uhrich et al. |
| 2005/0031577 A1 | 2/2005 | Uhrich et al. |
| 2005/0053577 A1 | 3/2005 | Uhrich et al. |
| 2005/0089504 A1 | 4/2005 | Uhrich et al. |
| 2005/0089506 A1 | 4/2005 | Uhrich et al. |
| 2005/0100526 A1 | 5/2005 | Uhrich et al. |
| 2005/0131199 A1 | 6/2005 | Uhrich et al. |
| 2005/0249697 A1 | 11/2005 | Uhrich et al. |
| 2006/0013851 A1 | 1/2006 | Giroux et al. |
| 2006/0039964 A1 | 2/2006 | Uhrich et al. |
| 2006/0057179 A1 | 3/2006 | Giroux et al. |
| 2007/0098800 A1 | 5/2007 | Giroux et al. |
| 2007/0196417 A1 | 8/2007 | Uhrich et al. |
| 2010/0152410 A1 | 6/2010 | East et al. |
| 2010/0291180 A1 | 11/2010 | Uhrich et al. |
| 2010/0291181 A1 | 11/2010 | Uhrich et al. |
| 2010/0310498 A1 | 12/2010 | Kanamathareddy et al. |
| 2011/0022161 A1 | 1/2011 | Uhrich et al. |
| 2012/0058155 A1 * | 3/2012 | Uhrich et al. .................. 424/400 |
| 2013/0022569 A1 | 1/2013 | Uhrich et al. |
| 2013/0071458 A1 | 3/2013 | Kanamathareddy et al. |
| 2014/0030341 A1 | 1/2014 | Uhrich et al. |
| 2014/0050692 A1 | 2/2014 | Uhrich et al. |
| 2014/0120057 A1 | 5/2014 | Uhrich et al. |

FOREIGN PATENT DOCUMENTS

| | | |
|---|---|---|
| JP | 51-134729 | 11/1976 |
| JP | 53-082743 | 7/1978 |
| JP | 56-007716 | 1/1981 |
| JP | 6255797 | 12/1985 |
| JP | 61186309 | 8/1986 |
| JP | 06-328857 | 11/1994 |
| JP | 07-149044 | 6/1995 |
| NL | 9000237 | 8/1991 |
| WO | WO 90/09779 | 9/1990 |
| WO | WO 91/09831 | 7/1991 |
| WO | WO 91/18940 | 12/1991 |
| WO | WO 97/39738 | 10/1997 |
| WO | WO 97/44016 | 11/1997 |
| WO | WO 97/49385 | 12/1997 |
| WO | WO 98/36013 | 8/1998 |
| WO | WO 98/43554 | 10/1998 |
| WO | WO 99/12990 | 3/1999 |
| WO | WO 99/29885 | 6/1999 |
| WO | WO 99/36107 | 7/1999 |
| WO | WO 00/12990 | 3/2000 |
| WO | WO 00/66730 | 11/2000 |
| WO | WO 01/28492 | 4/2001 |
| WO | WO 01/41753 | 6/2001 |
| WO | WO 02/09767 | 2/2002 |
| WO | WO 02/09768 | 2/2002 |
| WO | WO 02/09769 | 2/2002 |
| WO | WO 03/046034 | 6/2003 |
| WO | WO 03/065928 | 8/2003 |
| WO | WO 03/066053 | 8/2003 |
| WO | WO 03/072020 | 9/2003 |
| WO | WO 2004/006863 | 1/2004 |
| WO | WO 2004/039355 | 5/2004 |
| WO | WO 2004/045549 | 6/2004 |
| WO | WO 2005/039489 | 5/2005 |
| WO | WO 2005/042600 | 5/2005 |
| WO | WO 2006/127667 | 11/2006 |
| WO | WO 2007/143698 | 12/2007 |
| WO | WO 2008/034019 | 3/2008 |
| WO | WO 2008/103744 | 8/2008 |
| WO | WO 2008/128193 | 10/2008 |
| WO | WO 2009/026544 | 2/2009 |
| WO | WO 2012/139015 | 10/2012 |
| WO | WO 2014/194055 | 12/2014 |

OTHER PUBLICATIONS

Aebischer, P., et al., "Basic fibroblast growth factor released from synthetic guidance channels facilitates peripheral nerve regeneration across long nerve gaps", *Journal of Neuroscience Research*, 23(3), 282-289, (Jul. 1989).

Anastasiou, T.J., "Novel, Degradable Polyanhydrides", *25th Annual Meeting Transactions of the Society for Biomaterials*, Abstract, 79, (1999).

(56) References Cited

OTHER PUBLICATIONS

Anastasiou, T.J., "Novel Polyanhydrides with Enhanced Thermal and Solubility Properties", *Macromolecules*, 33(17), 6217-6221, (2000).

Anastasiou, T.J., "Synthesis of Novel, Degradable Polyanhydrides Containing Para-Aminosalicylic Acid as Drug Delivery Devices for Tuberculosis Treatment", *Polymer Preprints*, 41(2), 1366-1367, (Aug. 2000).

Arredondo et al., Effects of Linkers Substitution on Salicylic Acid-derived Poly(anhydride-esters), website of Rutgers, the State University of New Jersey, 16 pages (2001).

Attawia, M.A., "Biocompatibility Testing of Poly(anhydride-co-imides) Containing Pyromellitylimidoalanine", *The 21st Annual Meeting of the Society for Biomaterials*, Abstract, 222, (Apr. 5-9, 1994).

Attawia, M.A., "Cytotoxicity testing of poly(anhydride-co-imides) for orthopedic applications", *Journal of Biomedical Materials Research*, 29(10), 1233-1240, (1995).

Attawia, M.A., "In vitro bone biocompatibility of poly(anhydride-co-imides) containing pyromellitylimidoalanine", (1996). *Journal of Orthopedic Research*, 14(3), 445-454, (1996).

Attawia, M.A., "The Long Term Osteoblast Response to Poly(anhydride-co-imides): A New Degradable Polymer for Use in Bone", *Proceedings of the Fifth World Biomaterials Congress*, Toronto, Canada, 113, (1996).

Attawia, M.A., "Proliferation, Morphology, and Protein Expression by Osteoblasts Cultured on Poly(anhydride-co-amides)", *Journal of Biomedical Materials Research*, 48(3), 322-327, (1999).

Attawia, M.A., "Regional drug delivery with radiation for the treatment of Ewing's sarcoma—in vitro development of a taxol release system", *Journal of Controlled Release*, 71, 193-202 (2001).

Beaton, M.L., "Synthesis of a novel poly(anhydride-ester)", *The Rutgers Scholar—An Electronic Bulletin of Undergraduate Research*, 3, 1-7, (2001), http://www.scils.rutgers.edu/~weyang/ejournal/volume03/beatuhri/beatuhri.htm.

Bedell, C., "Processing and Hydrolytic Degradation of Aromatic, Ortho-Substituted Polyanhydrides", *Journal of Applied Polymer Science*, 80, 32-38, (2001).

Brambley, D., et al., "Microlithography: an overview", *Advanced Materials for Optics and Electronics*, 4(2), 55-74, (Mar.-Apr. 1994).

Branch, D.W., "Microstamp patterns of biomolecules for high resolution neuronal networks", *Medical & Biological Engineering & Computing*, 36(1), 135-41, (Jan. 1998).

Brown, J.P., "A Polymeric Drug for Treatment of Inflammatory Bowel Disease", *Journal of Medicinal Chemistry*, 26(9), 1300-1307, (1983).

Brown, L., et al., "Transdermal delivery of drugs", *Annual Review of Medicine*, 39, 221-9, (1988).

Campo, C.J., "Polyanhydrides: the effects of ring substitution changes on polymer properties", *Polymer Bulletin*, 42, 61-68, (1999).

Carbone et al., "Design and Synthesis of Fast-Degrading Poly(anhydride-esters)", *Macromol. Rapid Commun.*, 30, 1021-1026 (2009).

Chafi, N., "Dosage Form with Salicylic Acid Attached to the Polyanhydride Polymer Dispersed in an Eudragit Matrix", *International Journal of Pharmaceutics*, 52, 203-211, (1989).

Chatterjee, R., et al., "Mechanism for the Increase in Solubility of Deoxyhemoglobin S due to Cross-Linking the Beta Chains Between Lysine-82 Beta 1 and Lysine-82 Beta 2", *Biochemistry*, 21, 5901-5909, (1982).

Chen, G., "Effect of protein and cell behavior on pattern-grafted thermoresponsive polymer", *Journal of Biomedical Materials Research*, 42(1), 38-44, (Oct. 1998).

Conix, A., "New High-Melting Fibre-Forming Polymers", *Die Makromolekulare Chemie*, XXIV, 76-78, (1957).

Conix, A., "Aromatic Polyanhydrides, a New Class of High Melting Fiber-Forming Polymers", *Journal of Polymers Science*, XXIX, 343-353, (1958).

Conix, A., "Poly [1,3-bis (p carboxyphenoxy)—Propane anhydride]", *Macromolecular Synthesis*, 2, 95-99, (1996).

Cotlier, "Distribution of salicylate in lens and intraocular fluids and its effect on cataract formation", *American Journal of Medicine*, 74 (6A), 83-90 (1983).

Cotlier, "Senile Cataracts: Evidence for Acceleration by Diabetes and Deceleration by Salicytate", *Canadian Journal of Ophthalmology*. 16(3), 113-118 (1981).

Davaran, S., "Release of 5-amino Salicylic Acid from Acrylic Type Polymeric Prodrugs Designed for Colon-specific Drug Delivery", *Journal of Controlled Release*, 58(3), 279-287, (1999).

Davies, M.C., "The Analysis of the Surface Chemical Structure of Biomedical Aliphatic Polyanhydrides Using SPX and ToF-SIMS", *Journal of Applied Polymer Science*, 42, No. 6, New York, US, 1597-1605, (Mar. 20, 1991).

Delamarche, E., et al., "Patterned delivery of immunoglobulins to surfaces using microfluidic networks", *Science*, 276(5313), 779-781, (May 2, 1997).

Dewez, J.L., et al., "Adhesion of mammalian cells to polymer surfaces: from physical chemistry of surfaces to selective adhesion on defined patterns ", *Biomaterials*, 19(16), 1441-1445, (Aug. 1998).

Domb, A.J., "Polyanhydrides. I. Preparation of High Molecular Weight Polyanhydrides", *Journal of Polymer Science: Part A: Polymer Chemistry*, 25, 3373-3386, (1987).

Domb, A.J., "Synthesis and Characterization of Biodegradable Aromatic Anhydride Copolymers", *Macromolecules*, 25, 12-17, (1992).

Dontha, N., "Generation of biotin/avidin/enzyme nanostructures with maskless photolithography", *Analytical Chemistry*, 69(14), 2619-25, (Jul. 15, 1997).

Dukovic, G., "Novel degradable poly(anhydride-esters) for controlled drug release", *The Rutgers Scholar—An Electronic Bulletin of Undergraduate Research*, 1, 1-10, (1999), http://www.scils.rutgers.edu/~weyang/ejournal/volume01/uhriduko/uhriduko.htm.

Erdmann, L., "Polymeric Prodrugs with Pharmaceutically Active Degradation Products", *Polymer Preprints*, 38(2), 570-571, (1997).

Erdman et al., "Synthesis and Characterization of a Polymeric Prodrug", *Proceedings of the American Chemical Society Division of Polymeric Materials: Science and Engineering*, 78, Abstract Spring Meeting, Dallas, TX, pp. 194, (Apr. 1998).

Erdmann, L., et al., Chapter 5, "Polymeric Prodrugs: Novel Polymers with Bioactive Components", *In: Tailored Polymeric Materials for Controlled Delivery Systems*, I. McCulloh, et al., (Editors), ACS Symposium Series 709, Developed from a symposium sponsored by the Division of Polymer Chemistry at the 214th National Meeting of the American Chemical Society, Las Vegas, Nevada, Sep. 7-11, 1997, American Chemical Society: Washington, D.C., 83-91, (1998).

Erdmann, L., "Polymeric Prodrugs: Novel Polymers for Delivery of Salicylic Acid", *Annals of Biomedical Engineering*, 26 (Suppl. 1), Abstract No. PB.26, Annual Fall Meeting, S-124, (1998).

Erdmann, L., "Polymeric Salicylic Acid: In Vitro and In Vivo Degradation", *Polymer Preprints*, 39(2), 224-225, (1998).

Erdmann, L., "Degradable poly(anhydride ester) implants: effects of localized salicylic acid release on bone", *Biomaterials*, 21(24), 2507-2512, (2000).

Erdmann, L., "Synthesis and degradation characteristics of salicylic acid-derived poly(anhydride-esters)", *Biomaterials*, 21(19), 1941-1946, (Oct. 2000).

Giammona, G., "Polymeric Prodrugs alpha beta poly-hyroxyethyl-dl-aspartamide as macromolecular carrier for some non-steroidal anti-inflammatory agents", *Abstracts from Database BIOSIS Online, Biosciences Information Service*, Philadelphia, PA, Original Publication from the International Journal of Pharmaceutics (Amsterdam), 1 page (1989).

Giammona, G., "Polymeric Prodrugs Alpha Beta Poly-N-hydroxyethyl-DL-aspartamide as a Macromolecular Carrier for Some Non-Steroidal Anti-inflammatory Agents", *International Journal of Pharmaceutics*, 57, 55-62, (1989).

Gouin, S., et al., "New Polyanhydrides Made from a Bile Acid Dimer and Sebacic Acid: Synthesis, Characterization and Degradation", *Macromolecules*, 33, 5379-5383, (2000).

Harten et al., "Salicylic acid-derived poly(anhydride-esters) inhibit bone resorption and formation in vivo", *J Biomed Mater Res* 72A, 354-362 (2005).

(56) References Cited

OTHER PUBLICATIONS

Heasman et al., "The Effect of a Topical Non-Steroidal Anti-Inflammatory Drug on the Development of Experimental Gingivitis in Man", *J. Clin Periodontol* 16 (6), 353-358 (1989).
Heasman et al., "The use of topical flurbiprofen as an adjunct to non-surgical management of periodontal disease", *J. Clin Periodontol*, 20(6), 457-464 (1993).
Herbert, C.B., "Micropatterning gradients and controlling surface densities of photoactivatable biomolecules on self-assembled monolayers of oligo(ethylene glycol) alkanethiolates", *Chemistry & Biology*, 4(10), 731-7, (Oct. 1997).
Ibim, S., "Controlled Release Based on Poly(anhydride-co-imides)", *Proc. Intern. Symp. Control. Rel. Bioact. Mater.*, 22, 2 pgs, (1995).
Ibim, S.M., "Poly(anhydride-co-imides): In Vivo Biocompatibility in a rat model", *Biomaterials*, 19(10), 941-951, (1998).
Ibim, S.E., "Preliminary in vivo report on the osteocompatibility of poly(anhydride-co-imides) evaluated in a tibial model.", *Journal of Biomedical Material Research*, 43(4), 374-379, (Winter 1998).
Ito, Y., "Micropatterned immobilization of epidermal growth factor to regulate cell function", *Bioconjugate Chemistry*, 9(2), 277-82, (Mar.-Apr. 1998).
James, C.D., "Patterned Protein Layers on Solid Substrates by Thin Stamp Microcontact Printing", *Langmuir*, 14(4), 741-744, (1998).
Jeffcoat, "The Effect of Systemic Flurbiprofen on Bone Supporting Dental Implants", *Journal of American Dental Associate*, 126, 305-311 (1995).
Jeffcoat et al., "A comparison of topical ketorolac, systemic flurbiprofen, and placebo for the inhibition of bone loss in adult periodontitis", *J. Periodontol*, 66(5), 329-338 (1995).
Jiang, H.L., "Synthesis, Characterization and In Vitro Degradation of a New Family of Alternate Poly(ester-anhydrides) Based on Aliphatic and Aromatic Diacids", *Biomaterials*, 22(3), 211-218, (2001).
Jucker, M., et al., "Fetal rat septals cells adhere to and extend processes on basement membrane, laminin, and a synthetic peptide from the laminin A chain sequence", *Journal of Neuroscience Research*, 28(4), 507-17, (Apr. 1991).
Kleinfeld, D., "Controlled outgrowth of dissociated neurons on patterned substrates", *Journal of Neuroscience*, 8(11), 4098-120, (Nov. 1998).
Kompella et al., "(C) Means to Enhance Penetration: (4) Delivery Systems for Penetration Enhancement of Peptide and Protein Drugs: Design Considerations", *Advanced Drug Delivery Reviews* 8, Abstract Only, Obtained from http:/www.sciencedirect.com, 2 pages (Jan.-Feb. 1992).
Kompella et al., "Delivery systems for penetration enhancement of peptide and protein drugs: design considerations", *Advanced Drug Delivery Reviews*, vol. 46 (1-3), 211-245 (2001).
Kornman et al., "Effects of topical applications of meclofenamic acid and ibuprofen on bone loss, subgingival microbiota and gingival PMN response in the primate Macaca fascicularis", *J. Periodontal res.* 25(5), 300-307 (1990).
Krogh-Jespersen, E., "Synthesis of a Novel Aromatic Polyanhydride Containing Aminosalicylic Acid", *Polymer Preprints*, 41(1), 1048-1049, (2000).
Langer, R., "New Methods of Drug Delivery", *Science*, 249(4976), 1527-1533, (Sep. 1990).
Laurencin, C.T., "The Bone Biocompatibility of Poly(anhydride-co-imides)—A new generation degradable Polymer for Orthopedic Applications", 41st Annual Meeting of the Orthopedic Research Society, Orlando, FL, 143-24, (1995).
Laurencin, C.T., "Poly(anhydrides-co-imides): In Vivo Biocompatibility Study", *23rd Annual Meeting of the Society for Biomaterials*, New Orleans, LA, 483, (1997).
Laurencin, C.T., "The Biocompatibility of Poly(anhydride-co-imides): High Strength Polymers for Controlled Drug Delivery", *Proc. 24th Int'l Symp. Control. Rel. Bioact. Mater.*, 973-974, (1997).
Laurencin, et al., "The controlled delivery of radiosensitizers: taxol treatment for Ewing Sarcoma", *Proceedings of the 25$^{th}$ Int'l Symp. Control. Rel. Bioact. Mater.*, pp. 236-237, (1998).

Lawrence et al., "Pharmacokinetic and Safety Evaluations of Ketoprofen Gels in Subjects with adult periodontitis", *J. Dent Res.* 77(11), 1904-1912 (1998).
Lerner, "Indomethacin Inhibits Bone Resoprtion and Lysosomal Enzyme Release From Bone in Organ Culture", *Scandinavian Journal of Rheumatology, vol. 9* (3), 149-156 (1980).
Li et al., "The effect of ketoprofen creams on periodontal disease in rhesus monkeys", *J. Periodontal Res* 31(8), 525-532 (1996).
Longer, M.A., "Sustained-Release Drug Delivery Systems", *Remington's Pharmaceutical Sciences*, 18th Edition, Chapter 91, 1676-1693, (1990).
Macedo, B., et al., "The in vivo Response to a Bioactive Biodegradable Polymer", *Journal of Dental Research*, 78, Abstract No. 2827, 459, (1999).
Macedo, B., "The In Vivo Response to Bioactive Polyanhydride Monofilament", *Journal of Dental Research*, 79 (Abstract No. 3872), 627, (2000).
March, Advanced organic chemistry: reactions, mechanisms, and structure, 4$^{th}$ Edition, New York: Willey, 419-437 (1992).
Mountziaris et al., "Modulation of the Inflammatory Response for Enhanced Bone Tissue Regeneration" *Tissue Engineering*. 14, 179-186 (2008).
Pacios et al., "Diabetes aggravates periodontitis by limiting repair through enhanced inflammation", *FASEB Journal, vol. 26* (4), 1423-1430 (2012).
Paquette et al., "Enantiospecific inhibition of ligature-induced periodontitis in beagles with topical (s)-ketoprofen", *J. Clin Periodontol* 24(8), 521-528 (1997).
Pauletto et al., "Nonsteroidal antipinflammatory agents: potential modifiers of periodontal disease progression", *J. Can. Dent Assoc* 63(11), 824-829, 832 (1997).
Pinther, P., "Synthesis of Polyanhydrides Containing Ester Groups", *Die Makromolekulare Chemie, Rapid Communications*, 11(8), 403-408, (Aug. 1990).
Preshaw et al., "Periodontitis and diabetes: a two-way relationship", *Diabetologia* 55, 21-31 (2012).
Prudencio, A., "Biodegradable Polyanhydrides for Controlled Drug Release", Dissertation submitted to the Graduate School—New Brunswick, Rutgers, The State University of New Jersey, 228 pages (Oct. 2006).
Prudencio, A., et al., "A Novel Approach for Incorporation of Mono-Functional Bioactive Phenols into Polyanhydrides", *Macromolecular Rapid Communications*, 30, 1101-1108, 2009.
Prudencio et al., "Effect of Linker Structure on Salicylic Acid-Derived Poly(anhydride-esters)", *Macromolecules*. 38, 6895-6901 (2005).
Reynolds, et al., "Non-steroidal anti-inflammatory drug (NSAID)—derived poly(anhydride-esters) in bone and periodontal regeneration", *Current Drug Delivery*, 4(3), 233-239 (Jan. 1, 2007).
Rosario-Meléndez et al., "Stability of a Salicylate-based Poly(anhydride-ester) to Electron Beam and Gamma Radiation", *Polymer Degrad Stabil*. 96, 1625-1630 (2011).
Schacht, E., "Polymers for Colon Specific Drug Delivery", *Journal of Controlled Release*, 39, 327-338, (1996).
Schmalenberg, K., "Microlithographic patterning of polymer substrates for directed neuronal", *Polymeric Materials Science Engineering*, 81, Fall Meeting, Aug. 22-26, 1999, New Orleans, LA., 97, (1999).
Schmalenberg, K., "Patterned Polymer Substrates for directing Neuronal Growth", *ACS Regional Mid-Atlantic Research Meeting*, (1999).
Schmalenberg, K., "Patterning of polymer substrates for directed neuronal growth studies", *Laboratory for Surface Modification*, (Mar. 18, 1999).
Schmalenberg, K., "Thin Stamp Microcontact Patterned Printing of Protein Layers on Polymer Substrates", *Transactions: Twenty-Fifth Annual Meeting of the Society for Biomaterials*, Apr. 28-May 2, 1999.
Schmeltzer et al., "Optimized Synthesis of Salicylate-based Poly(anhydride-esters)", *Polymer Bulletin*. 49, 441-448 (2003).
Schmeltzer et al., "Synthesis and Cytotoxicity of Salicylate-Based Poly(anhydrideesters)", *Biomacromolecules*. 6, 359-367 (2005).
Seidel, J.O., "Erosion of Poly(anhydride-co-imides): A Preliminary Mechanistic Study", *J. Appl. Polym. Sci.*, 62(8), 1277-1283, (1996).

(56) References Cited

OTHER PUBLICATIONS

Shen, E., "Morphological Characterization of Erodible Polymer Carriers for Drug Release", *Proc. 26th Int'l Symp. Control. Rel. Bioact. Mater.*, 717-718, (1999).

Spargo, B.J., et al., "Spatially controlled adhesion, spreading, and differentiation of endothelial cells on self-assembled molecular monolayers", *Proceedings of the National Academy of Science USA*, 91(23), 11070-11074, (Nov. 8, 1994).

Sparks, et al., "Life after Union: Polymers-R-Us", Presentation at Union College, 40 pages (2007).

St. John, P.M., "Diffraction-based cell detection using a microcontact printed antibody grating", *Analytical Chemistry*, 70(6), 1108-11, (Mar. 15, 1998).

Swinyard, "Pharmaceutical Necessities", *In: Remington's pharmaceutical sciences by Joseph P. Remington; Alfonso R. Gennaro*, Easton, PA.: Mack Pub. Co.: ISBN: 0912734043, 1286-1329 (1990).

Tashiro, K., et al., "A synthetic peptide containing the IKVAV sequence from the A chain of laminin mediates cell attachment, migration, and neurite outgrowth", *Journal of Biological Chemistry*, 264(27), 16174-82, (Sep. 25, 1989).

Thomas et al., "Infection, Inflammation, and Bone Regeneration: a Paradoxical Relationship", *J Dent Res*. 90, 1052-1061 (2011).

Uhrich, K.E., "Synthesis and Characterization of poly(anhydride co-imides): Solution Polycondensation of Biodegradable Polymers Derived from Amino Acids", *Proc. of the American Chemical Society, Division of Polymeric Materials: Science and Engineering*, 70, Spring Meeting, San Diego, CA 239-240, (1994).

Uhrich, K.E., "Synthesis and Characterization of Degradable poly(anhydride-co-imides)", *Macromolecules*, 28(7), 2184-2193, (1995).

Uhrich, K.E., "Degradation of poly(anhydride-co-imides): Novel Polymers for Orthopedic Application", *Mat. Res. Soc. Symp. Proc.*, 394, 41-46, (1995).

Uhrich, K.E., "In Vitro Degradation Characteristics of Poly(anhydride-imides) Containing Pyromellitylimidoalanine", *J. Appl. Polymer Sci., Part A, Polym. Chem.*, 34(7), 1261-1269, (1996).

Uhrich, K.E., "In Vitro Degradation Characteristics of Poly(anhydride-imides) Containing trimellitylimidoglycine", *J. Appl. Polymer. Sci.*, 63(11), 1401-1411, (1997).

Uhrich, K.E., "Chemical Changes during in vivo degradation of poly(anhydride-imide) matrices", *Biomaterials*, 19(22), 2045-2050, (1998).

Uhrich, K.E., "Poly(anhydride-ester) Degradation: Mechanical Changes and Correlation to Antibiotic Release", *American Chemical Society, Abstracts of Papers, Part 2, Abstract No. 121*, $221^{st}$ ACS national Meeting, San Diego, CA, Abstract 121, (2001).

Uhrich, K.E., "Synthesis of Aminosalicylate-based polyanhydride Prodrugs: Esters, Amides, and Azos", *American Chemical Society, Abstracts of Papers, Part 2, Abstract No. 407*, 222nd ACS National Meeting, Chicago, IL, Abstract 407, (2001).

Uhrich, "Designing Polymers for Biomedical Applications", Presentation at Division of Engineering & Applied Science, Harvard University, Cambridge, MA, 50 pages (2002).

Uhrich et al., "Salicylate-Based Poly(Anhydride-Esters) for Protein Delivery", Presentation at POLY: Bioconjugate Polymers, ACS Meeting, Philadelphia, PA, 27 pages, Aug. 23, 2012.

Vogel et al., "The effects of a topically-active non-steroidal anti-inflammatory drug on ligature-induced periodontal disease in the squirrel monkey", *J. Clin. Periodontol*, 13(2), 139-144 (1986).

Wada et al., "Locally Delivered Salicylic Acid from a Poly(anhydride-ester): Impact on Diabetic Bone Regeneration", *J. Control Release* 171(1), 33-37- (2013).

Woo et al., "Synthesis and characterization of a novel biodegradable antimicrobial polymer", *Biomaterials*, 21, 1235-1246 (2000).

Woo, G.L., "Biological Characterization of a Novel Biodegradable Antimicrobial Polymer Synthesized with Fluoroquinolones", *J. Biomed. Mater. Res.* 59, 35-45, (2002).

Yagmurlu et al., "Sulbactam-Cefoperazone Polyhydroxybutyrate-co-Hydroxyvalerate (PHBV) Local Antibiotic Delivery System: In Vivo Effectiveness and Biocompatibility in the Treatment of Implant-Related Experimental Osteomyelitis", *Journal of Biomedical Materials Research* 46, 494-503 (1999).

Yazdi et al., "Effects of non-steroidal anti-inflammatory drugs on demineralized bone-induced bone formation", *Journal of Periodontal Research*, 27(1), 28-33, (Jan. 1992).

Yoda, N., "Synthesis of polyanhydrides. XII. Crystalline and high melting polyamidepolyanhydride of methylenebis(p-carboxybhenyl)amide", *Journal of Polymer Science*, 1, 1323-1338, (1963).

Zaugg, R.H., et al., "Modification of Hemoglobin with Analogs of Aspirin", *The Journal of Biological Chemistry*, 255(7), 2816-2821, (1980).

\* cited by examiner

A.

B.

A.

B.

A.

B.

under DE13207 awarded by the National Institutes of Health. The government has certain rights in the invention.

THERAPEUTIC COMPOSITIONS FOR BONE REPAIR

CROSS-REFERENCE TO RELATED APPLICATION

This application claims the benefit under 35 U.S.C. §119(e) of U.S. Provisional Application No. 61/793,507, filed Mar. 15, 2013, the entire contents of which is hereby incorporated by reference.

GOVERNMENT FUNDING

This invention was made with government support under DE13207 awarded by the National Institutes of Health. The government has certain rights in the invention.

BACKGROUND OF THE INVENTION

The loss of bone in the jaws from disease or trauma can be debilitating for patients. Clinicians have for many years depended on different materials to reconstruct the area. These have included bone from another part of the body, artificial materials, or processed bone from humans or animals. Many of these have disadvantages including limited amounts, concerns with disease transmission, inability to form the shape needed and low potential to regrow bone. In addition, recent studies have shown that bone healing in diabetes decrease the amount of newly formed bone.

Patients with diabetes are more prone to fractures, periodontitis, and other bone related issues as compared to healthy individuals. Current bone healing materials are less efficacious in diabetic patients than in non-diabetic patients; increased inflammation in diabetic patients is hypothesized to be a contributing factor. The chronic inflammation associated with diabetes disrupts normal bone physiology, inhibiting bone growth and causing bone resorption. Because of this, diabetic patients often have much longer healing times for fractures and have higher rates of non-integration with bone grafts. Diabetics require new bone repair methods that take this inflammation into account and reverse it to allow for improved healing.

SUMMARY OF THE INVENTION

In an aspect of the invention, there is provided a method for decreasing bone resorption or increasing bone formation or promoting bone healing at a site in the body of a diabetic mammal comprising administering at or near the site a biodegradable polymer comprising one or more groups in the polymer backbone, which upon hydrolysis of the polymer will yield a biologically active agent selected from the group consisting of a non-steroidal anti-inflammatory, an antibacterial (antibiotics), an analgesic, and an antioxidant.

In another aspect, there is provided a method for decreasing bone resorption or increasing bone formation or promoting bone healing at a site in the body of a diabetic mammal comprising, administering at or near the site a biodegradable polymer comprising one or more units of formula (I) in the backbone:

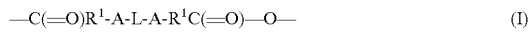

—C(=O)R¹-A-L-A-R¹C(=O)—O—     (I)

wherein each $R^1$ is a group that upon hydrolysis of the polymer is a biologically active agent selected from the group consisting of a non-steroidal anti-inflammatory, an antibiotic, an analgesic, and an antioxidant; each A is independently selected from the group consisting of esters, amides, urethanes, carbamates and carbonates; and each L is independently a linker molecule.

DETAILED DESCRIPTION

Figure 1:
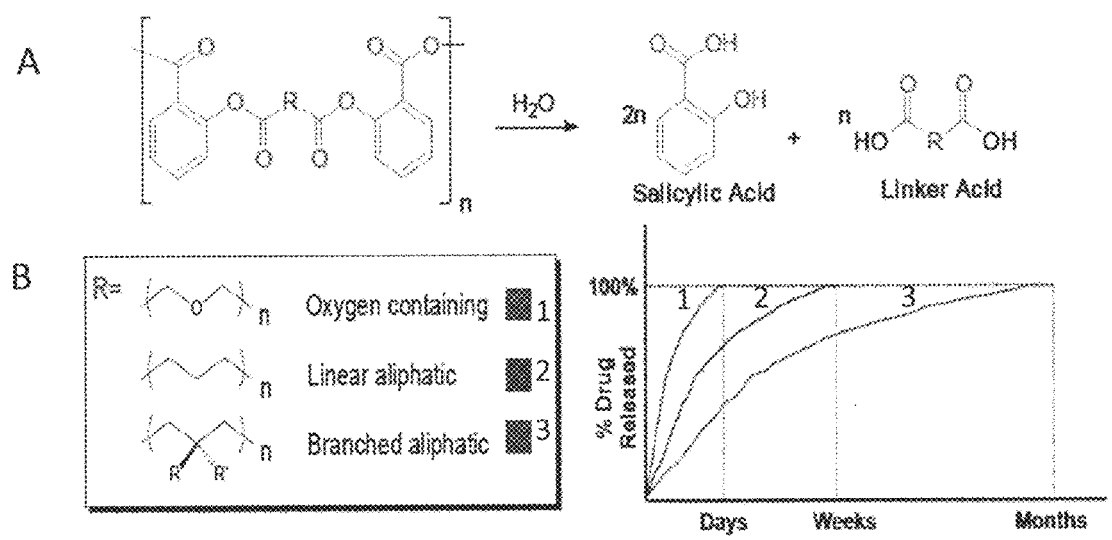
FIG. 1. A) Degradation scheme of a salicylate-based polyanhydride, wherein salicylic acid and a linker molecule are released in a controlled manner. While salicylic acid is shown in this illustration, other drugs may also be chemically incorporated into the polymer backbone. B) The chemical composition of the linker can vary the rate of drug release (e.g., days to months).
Figure 2:
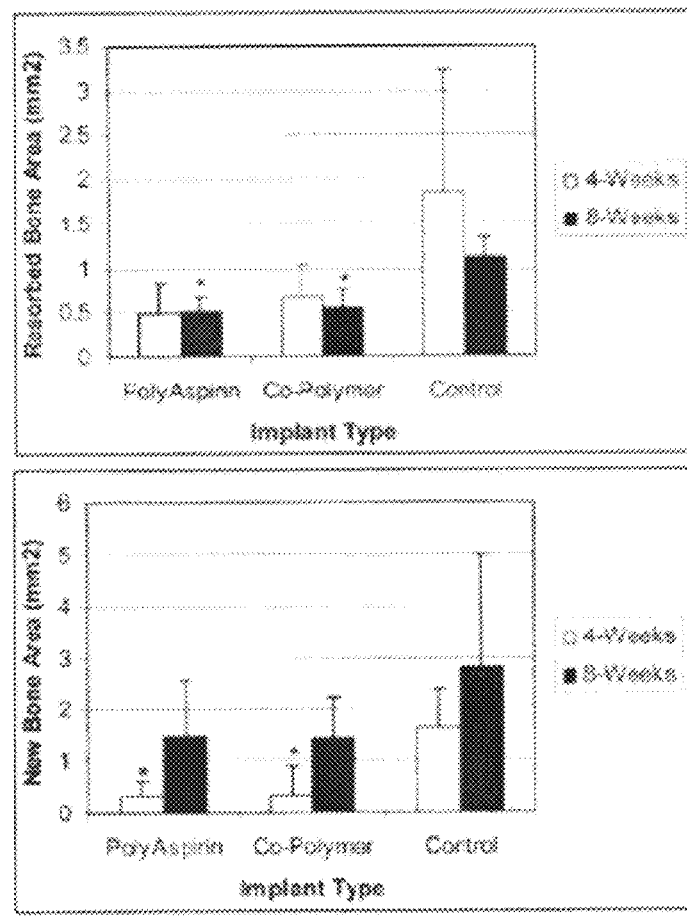
FIG. 2. Resorbed bone area at 4 and 8 weeks following treatment with polyaspirin incorporating sebacic acid linker (illustrated in FIG. 1A in which R=—($CH_2$)$_8$—), co-polymer of 50% polyaspirin with adipic linker and 50% 4-hydroxybenzoic acid and control.
Figure 3:
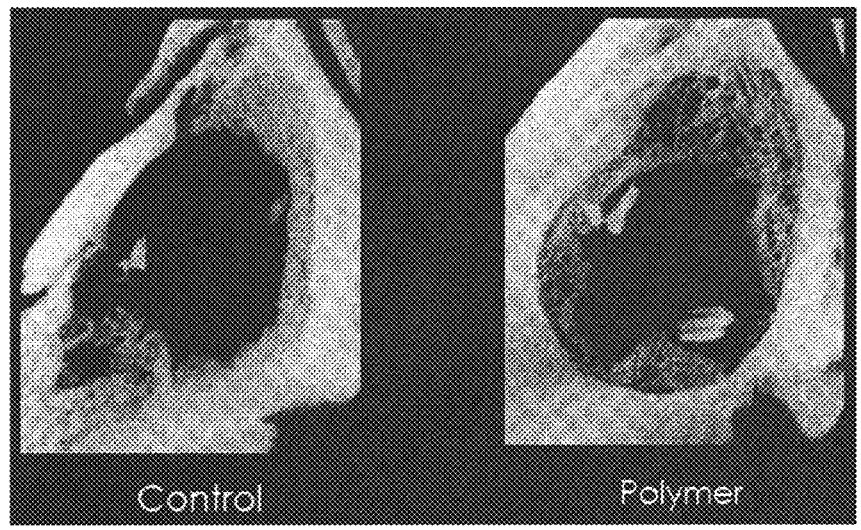
FIG. 3. A) μCT images of control and polyaspirin (adipic acid-linked, R=—($CH_2$)$_4$—, see, FIG. 1A) treated defects after 4 weeks. B) Average percent bone fill in defects after 4 weeks.
Figure 3:
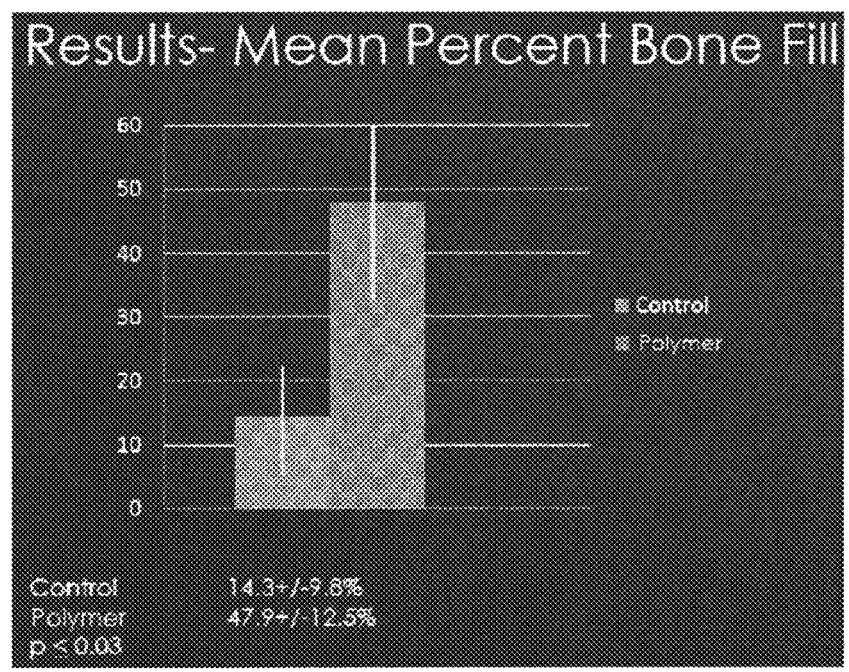
Figure 4:
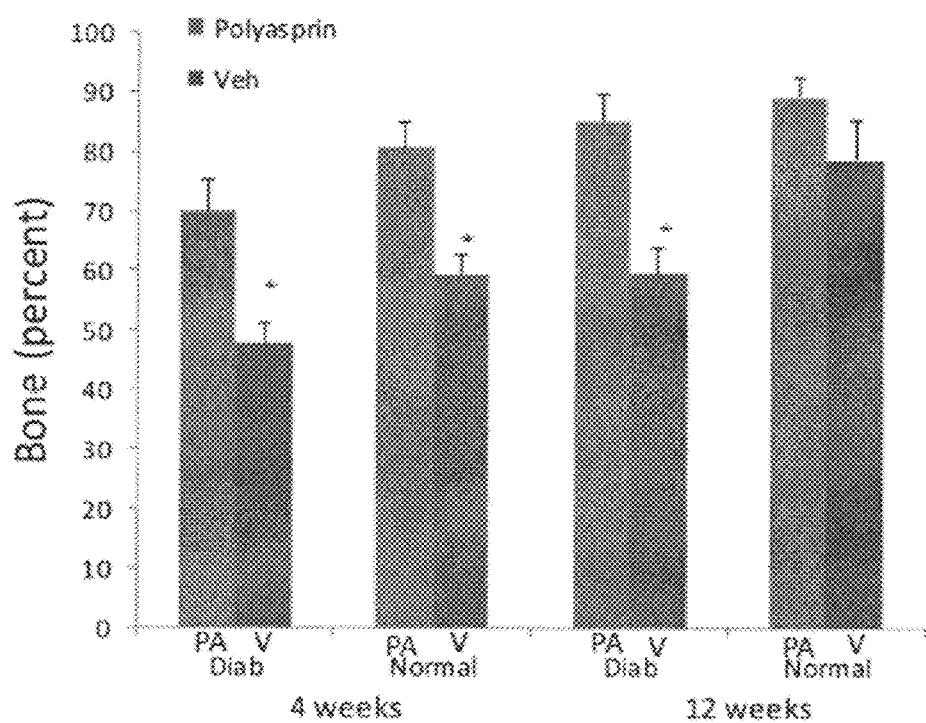
FIG. 4. Bone (%) at 4 and 12 weeks for diabetic and normal rats, which were administered either a mixture of bone graft and polyaspirin (adipic acid-linked, R=—($CH_2$)$_4$—) (left bar—P) or veh (bone graft alone) (right bar—V). Each value represents the mean of six specimens+standard error of the mean. * indicates p<0.05. Values were obtained by micro CT.

Diabetes is characterized by increased chronic inflammation, which can impair wound healing and lead to bone resorption. The localized release of drugs that reduce this inflammation may help bone healing in diabetic patients. Polymers that release therapeutic molecules (e.g., non-steroidal anti-inflammatory drugs (NSAIDs) and antibiotics) upon hydrolytic degradation have been developed. The controlled, sustained release of these drugs locally was examined in the studies described herein to determine whether they could improve bone repair for diabetic patients, as diabetes is characterized by increased inflammation and susceptibility to infection. This localized release avoids the side effects associated with systemic delivery of NSAIDs while maintaining therapeutically useful drug concentrations at the desired site.

The invention provided herein is based on the development of polymer, e.g., a poly(anhydride-ester) (PAE) of aspirin, and the observation that such polymers promote bone repair in diabetic patients with unexpected efficacy. The polymers, e.g. salicylate polymers that are aspirin based stimulate the body to regrow bone. In addition, they are easy to handle and shape, can be produced in unlimited amounts. Polyanhydrides, e.g., PAEs have enhanced processing properties and can maintain their structural integrity at physiological temperature. The raw polymer powder can be fabricated into many forms such as discs, films, coatings, and microspheres for a variety of applications. These polymers are surface eroding; therefore, geometries that increase surface area will also increase the rate of drug release. The drug release profiles can be controlled depending upon the formulation used and linkers chosen. Making copolymers with more than one type of linker, or with inactive monomers can also adjust drug release rate and loading.

Polymers of the invention that are salicylate-based polyanhydrides, e.g., PAEs are materials that have salicylic acid (SA), an NSAID, chemically incorporated into the polymer backbone via a biocompatible linker. This allows for very high drug loading, up to 75%. In the presence of water, the polymers degrade to release SA and the linker molecule in a controlled manner, with the chemical composition of the linker controlling the rate of drug release. Manipulation of the polymer composition allows complete release of the drug over the course of days to months. Other bioactives (e.g., antioxidants, antimicrobials, and other anti-inflammatory/analgesics) may also be chemically incorporated into these biodegradable polymers.

Studies have demonstrated that the localized release of salicylic acid from poly(anhydride-esters) may be beneficial for bone repair. The results from these studies indicate that the effect of the polymers is dose dependent. Erdmann et al. used small amounts of polymer, which resulted in increased bone formation and decreased bone resorption as compared to controls (37% more bone in treated group vs. control) (Biomaterials 21: 2507-2512, (2000)). Harten et al. used larger amounts of polymer that inhibited both new bone formation as well as bone resorption (*J Biomed Mater Res* 72A: 354-362 (2005)). These polymers also reduce inflammation and edema in the soft tissue surrounding treated bone (Reynolds, et al., *Current Drug Delivery.* 4: 233-239 (2007)). Bone treated with PAE maintain straight cuts on the bone while the control bone allows for new bone to form from the marrow (evident in CT scan) but also allows resorption (evident in both CT scan and histology slide).

The amount of drug necessary to promote the fastest healing may depend on the site and the specific conditions of the defect. The ability of these polymers to inhibit bone resorption would be especially beneficial for applications in which chronic inflammation is present, such as periodontitis, osteoarthritis, and diabetes where high amounts of inflammatory cytokines increase the activity of osteoclasts which in turn leads to bone resorption. For example, patients with diabetes are more prone to fractures, periodontitis, and other bone related issues as compared to healthy individuals. They also experience decreased rates of repair/resolution for these problems. Current bone healing materials are less efficacious in diabetic patients than in non-diabetic patients; increased inflammation in diabetic patients is believed to be the cause. This inflammation can inhibit bone growth and cause bone resorption. The invention provided herein specifically addresses this complication in diabetic bone repair. The polymers described herein, e.g., poly(anhydride-esters), have drugs chemically incorporated into the polymer backbone, which are released upon polymer degradation in a controlled manner. For example, the localized release of anti-inflammatories (e.g., salicylic acid) at a bone defect site could help diabetic patients by mitigating the factors, such as inflammation, that inhibits bone repair and causes their bone to resorb.

The localized release of antimicrobials can prevent the inflammation associated with bacterial infections. The polymers can also be used as a delivery device for additional bioactives (e.g., antibiotics, growth factors, etc.) by physically incorporating them within the polymer matrix to achieve a multi-release system for synergistic effect (e.g., improved bone growth). Additionally, the polymers described herein can be used alone or in combination with other polymers, drugs, growth factors (e.g., bone growth factors), and osteoconductive/osteoinductive materials to achieve greater effects. These polymers can also be used to coat other bone healing devices.

The polymer materials provided herein may be used to decrease bone resorption, promote bone formation and/or promote proper bone healing in diabetics, by e.g., mitigating inflammation locally.

In certain embodiments the polymer materials comprise a backbone selected from a branched aliphatic, linear aliphatic, and oxygen-containing linkers having the general formula (I):

$$-C(=O)R^1\text{-A-L-A-}R^1C(=O)-O-\qquad\text{(I)}$$

wherein each $R^1$ is a group that will provide a biologically active agent upon hydrolysis of the polymer; each A is independently an ester, amide, carbamate or carbonate group; and each L is independently a linker molecule.

In certain embodiments, L is adipic ($-CH_2CH_2CH_2CH_2-$) or diethylmalonic ($-CH_2C(Et)_2CH_2-$).

In certain embodiments L is adipic ($-CH_2CH_2CH_2CH_2-$).

In certain embodiments, L is diethylmalonic ($-CH_2C(Et)_2CH_2-$).

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by ($-O-$), ($-NR-$) or phenylene, and wherein the chain is optionally substituted on carbon with one or more (e.g. 1, 2, 3, or 4) substituents selected from the group consisting of ($C_1$-$C_6$)alkoxy, ($C_3$-$C_6$)cycloalkyl, ($C_1$-$C_6$)alkanoyl, ($C_1$-$C_6$)alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy, wherein each R is independently selected from H or $(C_1-C_6)$alkyl.

In certain embodiments, L is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

In certain embodiments, L is a peptide.

In certain embodiments, L is an amino acid.

In certain embodiments, L is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—), (—NR—) or phenylene, wherein each R is independently selected from H or $(C_1-C_6)$alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy, wherein each R is independently selected from H or $(C_1-C_6)$alkyl.

In certain embodiments, L is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—), (—NR—) or phenylene, wherein each R is independently selected from H or $(C_1-C_6)$alkyl.

In certain embodiments, L is a divalent, branched or unbranched, saturated or unsaturated, hydrocarbon chain, having from 3 to 15 carbon atoms.

In certain embodiments, L is a divalent, branched or unbranched, hydrocarbon chain, having from 3 to 15 carbon atoms.

In certain embodiments, L is a divalent, branched or unbranched, hydrocarbon chain, having from 6 to 10 carbon atoms.

In certain embodiments, L is a divalent hydrocarbon chain having 7, 8, or 9 carbon atoms.

In certain embodiments, L is a divalent hydrocarbon chain having 8 carbon atoms.

In certain embodiments, L is a divalent hydrocarbon chain having 4 carbon atoms.

In certain embodiments, $R^1$ is a non-steroidal anti-inflammatory compound. In a particular embodiment, $R^1$ is salicylic acid. In certain embodiments, the non-steroidal anti-inflammatory is salicylic acid, diflunisal, or salsalate. In a particular embodiment, $R^1$ is salicylic acid.

In a particular embodiment, $R^1$ an antibiotic.

In a particular embodiment, $R^1$ an analgesic. In certain embodiments, the analgesic is oxymorphone, buprenorphine, butorphanol, nalbuphine, orthocaine or salicyl alcohol.

In a particular embodiment, $R^1$ and an antioxidant compound. In certain embodiments, the antioxidant is ferulic acid, sinapic acid, or coumaric acid (e.g., p-coumaric acid).

In certain embodiments, A is an ester linkage. In another embodiment, A is an amide linkage. In another embodiment, A is a urethane linkage. In another embodiment, A is an carbamate linkage. In another embodiment, A is an carbonate linkage.

In certain embodiments, the polymers used in the methods of the invention have an average molecular weight of about 1,500 to 50,000 daltons. In a particular embodiment, polymers have an average molecular weight of about 1,500 to 35,000 daltons. In a particular embodiment, the polymer is a polyanhydride having an average molecular weight of about 1,500 to about 35,000 daltons calculated by Gel Permeation Chromatography (GPC) relative to narrow molecular weight polystyrene standards.

In certain embodiments, a second biologically active agent is dispersed in the matrix of the polymer or appended to the polymer backbone. In certain embodiments, the second biologically active agent is a non-steroidal anti-inflammatory, an antibacterial, an analgesic, an antioxidant or a growth factor. In certain embodiments, the second biologically active agent is the same as the biologically active agent in the polymer backbone. In certain embodiments, the second biologically active agent is different from the biologically active agent in the polymer backbone.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Typically, compounds of the invention will be administered as an implant at or near the site of a bone defect. For example, the compounds are mixed with bone graft (scaffold) and the resulting composition is administered at the site of a bone defect (see, e.g., the Examples). In certain embodiments, the bone graft is bone allograft (e.g., freeze-dried bone allograft). In certain embodiments, the bone graft is autologous. In certain embodiments, the composition further comprises mineral oil. The compound or mixture composition may be part of an implantable device that releases immediately or slowly.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for reducing inflammation and/or promoting bone healing. Examples of such anti-inflammatory agents include NSAIDs and anti-inflammatory steroids. Examples of such agents for promoting bone healing are bis-phosphophonates, hormones such as PTH and growth factors such as BMP. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to promote bone healing.

The invention will now be illustrated by the following non-limiting Examples.

Example 1

In Vitro Release Kinetics

Figure 5:
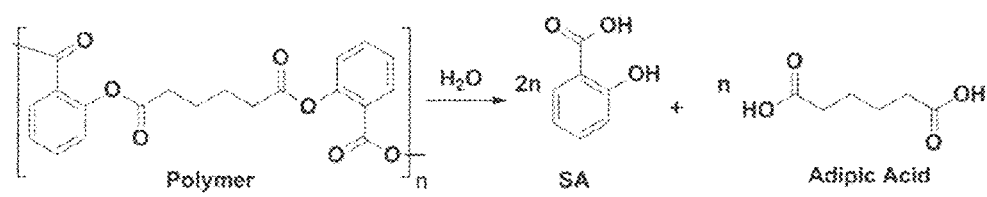
FIG. 5. A. PolySAA degradation scheme. Polymer degradation releases salicylic acid (SA) and adipic acid upon anhydride and ester bond hydrolysis. B. In vitro release profile of polySAA/bone graft/mineral oil. In vitro SA release from formulated samples (SA±standard error) over 21 days.
Figure 5:
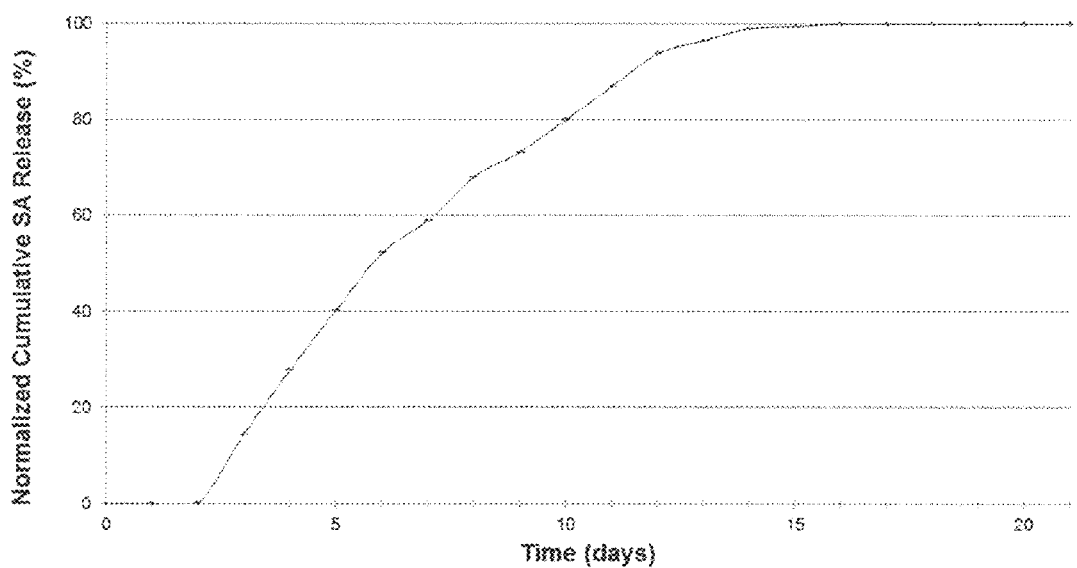

An implantable paste for in vitro drug release was prepared by adding bone graft (7.5 mg, Oragraft®) to polymer (salicylic acid-based poly(anhydride-ester) with an adipic linker) (7.5 mg). Two drops of mineral oil were added and the contents physically mixed together. This was performed in triplicate. Samples were then transferred to Wheaton glass scintillation vials. Samples were subjected to UV radiation for 1500 seconds in a UV chamber to sterilize samples. After sterilization, 10 mL phosphate buffered saline (PBS) at pH 7.4 was added. Samples were incubated at 37° C. with agitation at 60 rpm in a controlled environment incubator shaker (New Brunswick Scientific Co., Excella E25, Edison, N.J.). All media was collected and replaced with fresh PBS (10 mL) every 24 hours for 21 days. Spent media was analyzed by UV spectrophotometry using a Perkin Elmer Lambda XLS spectrophotometer (Waltham, Mass.) to specifically monitor SA release. Measurements were obtained at $\lambda=303$ nm, the maximum absorbance of salicylic acid (SA) that did not overlap with other polymer degradation products. Data were calculated against a calibration curve of absorbance values from standard solutions of known SA concentrations in PBS. For example, FIG. 5B shows the percent of cumulative SA release over time from UV sterilized samples from a similar experiment described in Example 4.

Example 2

In Vivo Bone Growth in Non-Diabetic Rats

Salicylic acid-based poly(anhydride-esters) were combined with demineralized bone allograft and mineral oil as described above and implanted into 60 non-diabetic rat mandible defects. The surgically created defect with 5 mm in diameter on the rat mandible has been well established as a critical size and used in many studies to evaluate the graft material for bone regeneration. Specifically, 40-day old Adult male Sprague-Dawley rats (weight 250-300 g each) were randomly assigned to a polymer treatment group or control group. These experiments used a through and through small (e.g. 5 mm diameter defect) in the angle of the rat mandible. Post-operative analysis involved micro computed tomography (micro CT) of the resulting new bone formation that occurs within the surgically created defect. The surgical technique and analysis were used to evaluate the efficacy of salicylate polymers as a treatment for enhancing bone regeneration. At the 28 day time point, the animals were sacrificed using $CO_2$ inhalation followed by decapitation in a chamber appropriate for the species. The mandibular tissues were retrieved and examined for bone formation with micro CT scan.

Animals were housed one or two per cage with ad lib food and water. Clean bedding was provided twice per week or more often to maintain hygiene. Animals were observed for activity, behavior, food intake, pain and weighed twice a week to monitor weight gain. Animals with letharge, dehydration, or poor weight gain/loss (e.g., >10% baseline weight loss (adults) or age-appropriate weight (juveniles)) were euthanized.

The surgeons wore a gown, mask, hair cover and sterile gloves before they entered into the surgical suite. Animals were anesthetized with an intraperitoneal injection of Ketamine, 75 mg/kg (Fort Dodge laboratories, Fort Dodge, Iowa) and Xylazine, 5 mg/kg (Miles Inc., Shawnee Mission, Kans.). After the skin on the mandible was shaved, the surgical site was clipped, then, scrubbed with a povidone-iodine scrub (e.g., Betadine®) and 70% alcohol, being careful to scrub from the center of the site toward the periphery. The site was then disinfected with povidone-iodine solution. A 2-cm superficial skin incision was made on the lower border of the mandible. The superficial fascia and muscles were separated, exposing the angle of the mandible under magnification. The site was irrigated with saline and a standardized 5 mm diameter circular defect was created with a trephine bur. The full thickness (~1.5-2 mm) of the mandibular bone was removed, and a scaffold (salicylate polymers (50 mg/kg) was immediately placed in the defect. In the experimental groups, the test treatments were placed. In the control "no treatment" group, the wound was simply rinsed. Flap management included replacement of the muscle. The surgical site was closed with 4-0 Vicryl®. The non resorbable sutures were removed with appropriate wound healing at 7-10 days post-surgery.

During the immediate post-operative period the animal was kept warm using lamp on paper towel in a clean bedded cage, and under close observation within the laminar-flow hood. After recovering, by exhibiting righting reflex, the animals were returned to the housing room. Metacam (2 mg/kg) and buprenorphine (0.05 mg/kg) were used subcutaneously for 2 to 3 days postoperatively, starting with recovery. The operator attended to the rats until the animals were fully recovered from the anesthesia (~45 min.) to make sure that they eat and drink normally. The diet was composed of soften chow. The possible post-operative pain was inferred by the absence of normal behaviors (alertness, mobility, groomed coat, good appetite and general condition).

The mandibles were harvested 28 days after surgery and analyzed by micro computerized tomography (µCT) for new bone formation. Polymer treated animals exhibited significantly greater new bone growth than controls. Similar in vivo studies using a diabetic rat model are described below.

Example 3

In Vivo Bone Growth in Diabetic Rats

In vivo bone growth was also compared in normal and diabetic rats using the salicylate polymer composition described above. Specifically, diabetes was induced by a single intraperitoneal injection of streptozotocin 70 mg/kg (The Upjohn Co., Kalamazoo, Mich.); streptozotocin-induced diabetic rats share many similarities to human type I diabetes. Dextrose was placed in the animals' water with the first 3 days after the induction with streptozotocin. Blood glucose was monitored by the glucose-oxidase method (Glucometer EncoreM, Miles Inc., Elkhart Ind.) two times a week to prevent too high a Glucose level. Glucose levels greater than 250 mg/dl was considered diabetic; diabetic levels were maintained for 3 weeks prior to surgery. 40-day old Adult male Sprague-Dawley rats (weight 250-300 g each) were randomly assigned to treatment groups. The surgical mandibular defect was performed and evaluated as described above. Animals were observed for activity, behavior, food intake, pain and non-healing diabetic ulcers daily and weighed twice a week to monitor weight gain. Diabetic animals should have a weekly weight gain of 2-5 grams. Animals with lethargy, dehydration, non-healing ulcers or poor weight gain/loss (e.g., >10% baseline weight loss (adults) or age-appropriate weight (juveniles)) were euthanized. At either the 4 week or 12 week time point, the animals were sacrificed using $CO_2$ inhalation followed by decapitation in a chamber appropriate for the species. The mandibular tissues were retrieved and examined for bone formation with micro CT scan.

Example 4

Effects of Salicylic Acid Released from Poly(Anhydride Ester) in Bone Regeneration in Normal and Diabetic Rats Abstract Diabetes Mellitus (DM) involves metabolic changes that can negatively influence wound healing resulting in impaired bone repair. A salicylic acid polyanhydride ester (polyaspirin) promotes controlled release of salicylic acid and reduces inflammation. This study, as described herein, investigated the effect of polyaspirin on bone regeneration under normal conditions and under conditions where there is enhanced inflammation caused by diabetes mellitus (DM). Fifty-six sprague-dawley rats were randomly assigned to two groups: DM induced by streptozotocin (STZ) or normoglycemic control injected with vehicle alone, citrate buffer. Three weeks after development of hyperglycemia, 5 mm diameter critical size defects were created at the rat mandibular angle and treated with polyaspirin combined with bone allograft or bone allograft alone. Rats were euthanized 4 weeks and 12 weeks later and the percentage of defect fill was assessed both by histomorphometry and by micro CT. There was significantly increased bone fill observed in polyaspirin treated diabetic rats compared to the bone graft alone at 4 weeks and 12 weeks. In normoglycemic rats, there was accelerated bone fill at 4 weeks but at 12 weeks polyaspirin and vehicle alone groups were similar. Accordingly, it was determined that treatment with polyaspirin enhances bone regeneration in diabetic rats and accelerates it in normoglycemic animals.

Introduction

Diabetes mellitus (DM) is a common metabolic disorder associated with hyperglycemia and hyperlipidemia due to lack of insulin or due to insulin resistance. In 2011 the prevalence of DM affected 8.3% of the U.S. population. DM represents a considerable health problem with significant morbidity and mortality. DM has been shown to increase systemic inflammation and to increase and prolong the inflammatory response to perturbation. The increased inflammation may be due to a number of different causes including the formation of reactive oxygen species, advanced glycation end products, hypoinsulinemia or insulin resistance.

Type 1 diabetes causes osteopenia and both type-1 and type-2 diabetes have been linked to poorer quality bone formation and reduced capacity to form bone. There are a number of factors that may contribute to this deficit including decreased expression of transcription factors that are needed to regenerate bone and the effect of inflammation on the expression of growth and differentiation factors needed to form bone as well as diminished vascularity. Furthermore, diabetes-enhanced inflammation has also been linked to prolonged osteoclastogenesis that may reduce bone quality.

Bone grafting is used to treat orthopedic and oral-facial defects. However in diabetes, the result of bone regeneration procedure have demonstrated lower predictability, and a greater degree of variability and increased infection rates. A number of approaches have been used to enhance the success rate of osseous healing and regeneration. Through the use of growth factors, hormones, or extracellular matrix proteins to stimulate cell chemotaxis, differentiation and growth, improved bone regeneration may be expected. Specifically, the use of growth factors has been tested and found to be significant for bone regeneration. However, limitations in the use of growth factors such as recombinant human bone morphogenetic proteins (BMP) have been reported in medically compromised patients and their high cost may limit clinical application.

Polyaspirin has recently been synthesized combining polyanhydride polymer and salicylic acid (Erdmann, et al., *Biomaterials* 2000, 21, (19), 1941-6). This method of delivery allows the development of an initial inflammatory response but through delayed degradation of the polymer facilitates a controlled and prolonged release of aspirin. This controlled release has many benefits. One is that the initial inflammatory response occurs normally allowing the development of a vigorous host response as well as the generation of factors that are needed to recruit mesenchymal stem cells needed for subsequent repair. The resolution of inflammation is also an important aspect of repair mediated by the generation of anti-inflammatory cytokines, binding proteins such as soluble receptors and lipid based anti-inflammatory mediators. Aspirin participates in the resolution of inflammation largely through the generation of resolvins. Because aspirin generates the production of anti-inflammatory lipid based mediators that promote resolution of inflammation and previous findings that diabetes impairs the formation of new bone because of diabetes-enhanced inflammation, the effect of a polyaspirin polymer on bone regeneration in diabetic rats was tested. The results indicate that polyaspirin treatment significantly promotes new bone formation in diabetic animals and accelerates new bone formation in normoglycemic counterparts.

Material and Methods

Graft Preparation.

Salicylic acid-derived poly(anhydride-ester) was synthesized using previously reported methods (Schmeltzer, et al., *Polymer Bulletin* 2003, 49, 441-448). The polymer was formulated in beads of 40 to 70 microns diameter and mixed with freeze-dried bone allograft (FDBA) obtained from LifeNet Health® (Virginia Beach, Va.) at a 50:50 weight ratio. Approximately 100 µl light mineral oil [Sigma-Aldrich, Milwaukee] was added to the mixture and sterilized under UV light at λ=254 nm for 900 s. Control samples were prepared without polymer and treated identically to the polymer containing samples.

Animal Model.

Animal care and surgical procedures were approved by the IACUC of the University of Pennsylvania. Fifty six adult male sprague-dawley rats weighing between 250 g to 350 g were used, n=7 per group. The rats were randomly divided into diabetic and non-diabetic groups. Diabetes was induced by intraperitoneal injection of streptozotocin [Sigma-Aldrich, Milwaukee] (70 mg/kg). Blood glucose was monitored by the glucose-oxidase method (Glucometer Encore, Miles, Elkhart, Ind.) and HbA1c was measured at the time of euthanasia. A blood glucose level greater than 250 mg/dL was considered diabetic. Animals were monitored during 3 weeks to confirm they maintained their diabetic status, and to evaluate their daily food intake and activity, their weight, and their overall health. The HbA1c level at sacrifice (4 weeks and 12 weeks) in the diabetic group is shown in Table 1 below. Of the 56 rats that underwent surgery, two rats died during the procedure. No significant reductions in body weight and 3 post-operative infections were observed.

TABLE 1

HbA1c levels in streptozotocin induced diabetes (n = 6)

| 4 weeks | 12 weeks |
|---|---|
| 11.76 ± 1.01 | 10.78 ± 1.16 |

Values are given as mean ± SD

Surgical Procedure.

All procedures were performed under general anesthesia with an intraperitoneal injection of ketamine, 75 mg per kg (Fort Dodge Laboratories, Fort Dodge, Iowa) and xylazine, 5 mg per kg (Miles Inc., Shawnee Mission, Kans.). Surgical procedures were performed under sterile conditions. A 15 to 20 mm incision was made on the lateral aspect of the mandible. A 5 mm diameter osteotomy defect was created at the angle of the mandible using a trephine burr with sterile saline irrigation. The site was grafted with freeze dried bone allograft (Virginia Beach, Va.) or polyaspirin-bone graft mixture. A BioGide® resorbable collagen membrane (Geistlich Pharma., North America Inc., New Jersey USA) was adapted to cover the defect circumferentially. The surgical field was closed in layers, a muscular layer and the external skin layer, using Chromic gut 5-0 resorbable sutures (Ethicon, Somerville, N.J.). A single dose of buprenorphine (0.05 mg/kg) and were administered for postoperative pain relief. Rats were euthanized at 4 and 12 weeks. The mandibles were dissected and fixed in 4% phosphate buffered formalin solution for 24 hours then stored with PBS until micro CT scan was performed.

Micro-Computed Tomography.

Micro-CT images were obtained using a eXplore Locus SP micro CT scanner (GE Healthcare, Pittsburgh, Pa.). Images were taken at a resolution of 48 microns. The micro-CT data sets were achieved and reconstructed with the GE software (GE Healthcare, Pittsburgh, Pa.) and the evaluated by OsiriX 64 image analysis software (Pixmeo, Geneva, Switzerland). The original circular defect was located, and a 3-D region of interest (ROD measuring 5.0 mm in diameter and 0.3 mm in height was established for the original defect. A bone/no-bone threshold value in CT Hounsfield units (HU) was determined and used to measure the amount of new bone present in the osteotomy defect. For each specimen, new bone formation was expressed as a percentage of defect closure in the 5.0 mm diameter defect.

Histologic Analysis.

After micro-CT specimens were demineralized with 10% EDTA (Fisher scientific USA, Pittsburgh, Pa.), which was changed three time weekly for 5 weeks. The specimen was cut in half after decalcification, embedded in paraffin and sectioned at the midline of the defect. 5 µm histologic sections were prepared and stained with hematoxylin and eosin. Histologic analysis was performed by a computer-digitized image analysis system: NIS Elements software (Nikon, Melville, N.Y.) and the percent bone fill of the defect was assessed. One half of the defect was analyzed and the area of new bone formation within the defect on one side by the total area of bone of half the defect (2.5 mm length) on that same side.

Statistical Analyses.

The data are presented as mean±SD. The difference between diabetic and normoglycemic groups at each time point was analyzed by Student's T-test. Significance was determined at $P<0.05$.

Results

In Vitro Salicylate Acid Release from Polyaspirin Graft.

Previously, the SA release profile of PA alone has demonstrated that PA degradation occurs via hydrolysis of anhydride and ester bonds to release therapeutic SA and biocompatible adipic acid (FIG. 5A). The new formulation described herein investigates the addition of bone graft and mineral oil to PA, both of which may have an effect on SA release from PA. In vitro studies were performed in PBS over 21 days using this new formulation and analyzed by UV spectrophotometry to ascertain the release profile. The normalized, cumulative SA release curves are depicted in FIG. 5B, where SA release began after day 2 following a lag period of no SA release. Near zero-order release was observed from days 3-16, which is common for polyanhydrides and poly(anhydride-esters) due to their surface-eroding behavior. These results demonstrate that this novel formulation sustained SA release over 16 days.

Bone Fill of Osteotomy Defect.

Figure 6:
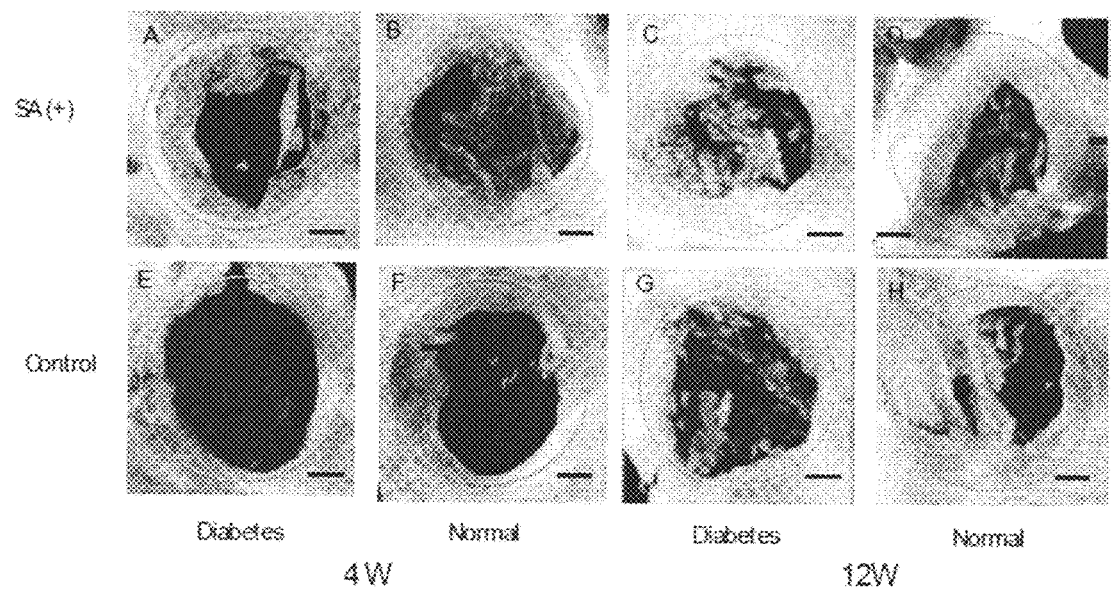
FIG. 6. A) Quantitative Comparison in bone formation analyzed by μ-CT. Representative μ-CT images of mineralized bone formation in 5 mm diameter critical size defects (gray circle on each image) implanted with SA/bone scaffold (A, B, C, D) and bone scaffold only (E, F, G, H) in diabetes and normal condition respectively after 4 and 12 weeks (bar=1 mm). "SA" is used in this figure to denote the polymer illustrated in FIG. 5A comprising salicylic acid (SA) and an adipic linker (—($CH_2$)$_4$—). B) Bone fraction with the original defect. Quantitative Comparison in bone formation within the defect analyzed by μ-CT. Data are presented as mean±SD analyzed by paired T test (n=6, *P<0.05).
Figure 6:
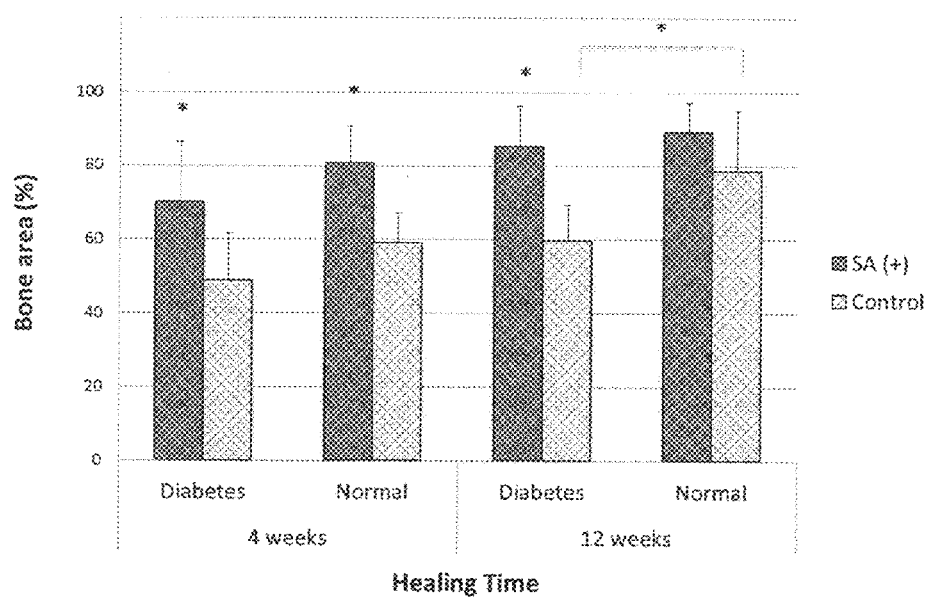
Figure 7:
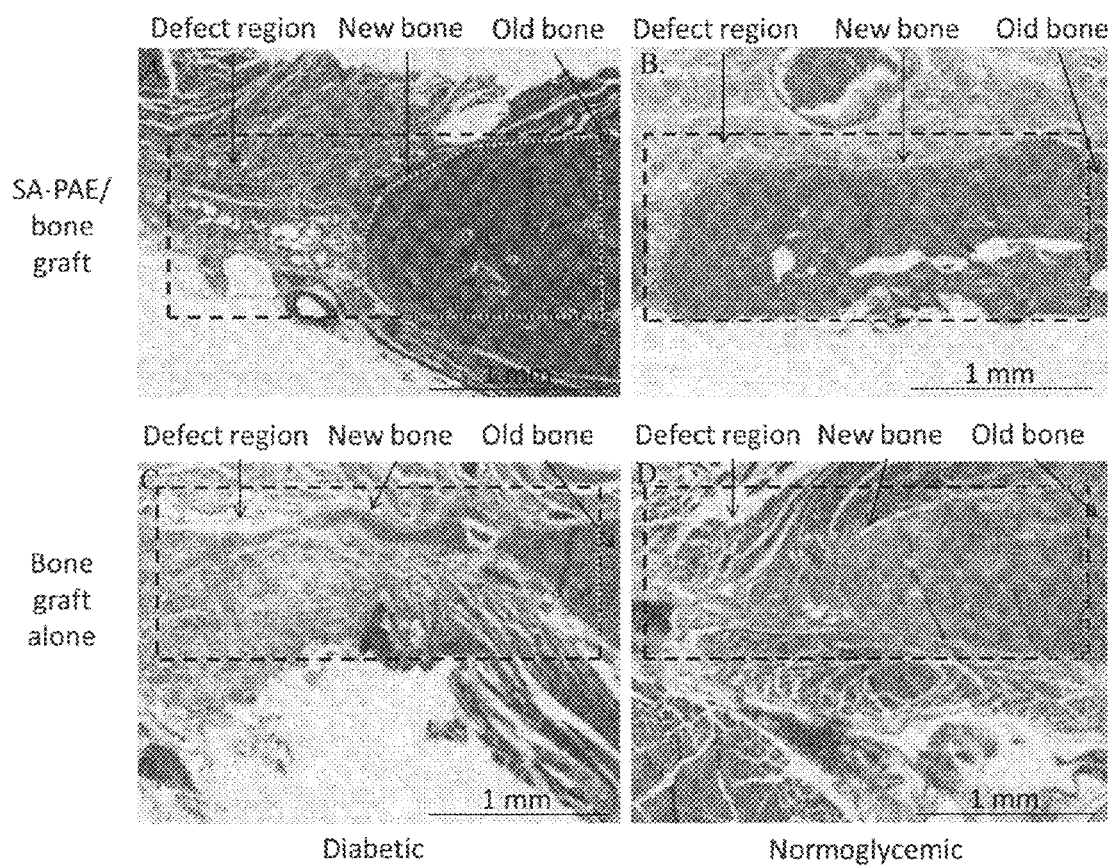
FIG. 7. Representative HE staining bone formation. Representative H&E staining demonstrating new bone matrix deposition within defects implanted with SA/bone scaffold (A, B) and bone scaffold only (C,D) in diabetes and normal condition respectively. (bar=1 mm). "SA" is used in the this figure to denote the polymer illustrated in FIG. 5A comprising salicylic acid (SA) and an adipic linker (—($CH_2$)$_4$—).

The amount of bone in the osteotomy defect was measured for each group by micro CT (FIG. 6A). At the 4 week time point the amount of bone fill in the normoglycemic control rats (bone graft alone) was statistically similar to the diabetic control rats ($p>0.05$). When diabetic rats were treated with polyaspirin there was 43.6% greater bone fill observed than diabetic rats treated with bone graft alone ($P<0.05$). Surprisingly an increase was also noted in the normoglycemic group with a 36.5% greater bone fill in the osteotomy defect with polyaspirin than bone graft without polyaspirin ($P<0.05$).

At 12 weeks the amount of bone in the normoglycemic control group with bone graft alone was 31.6% greater than the diabetic control group ($P<0.05$). When treated with polyaspirin plus bone graft the diabetic group had 42.7% greater bone fill than the diabetic treated with bone graft alone ($P<0.05$). However there was no significant difference between the polyaspirin plus bone graft and bone graft alone groups in normoglycemic rats ($P>0.05$).

Histologic Analysis.

Figure 8:
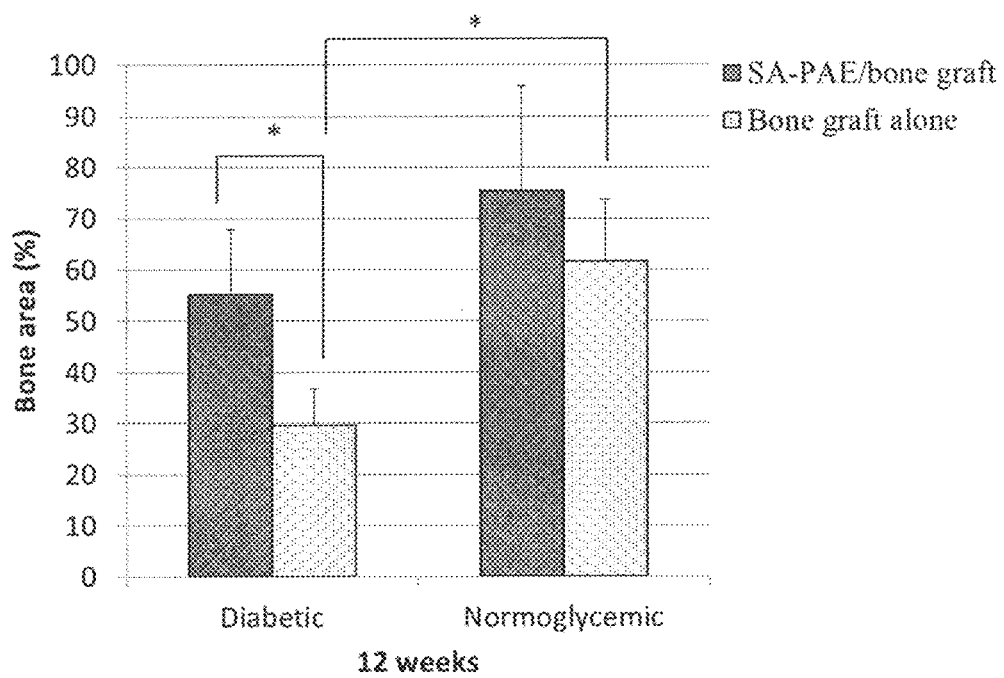
FIG. 8. Histomorphometric comparison of new bone fraction. Histomorphometric comparison of new bone fraction within the critical defect at 12 weeks of healing with mixture of bone graft and polyaspirin (with adipic linker (—($CH_2$)$_4$—) as shown in FIG. 5A) and control (bone graft only). Data are presented as mean±SD. (n=6).
Figure 9:
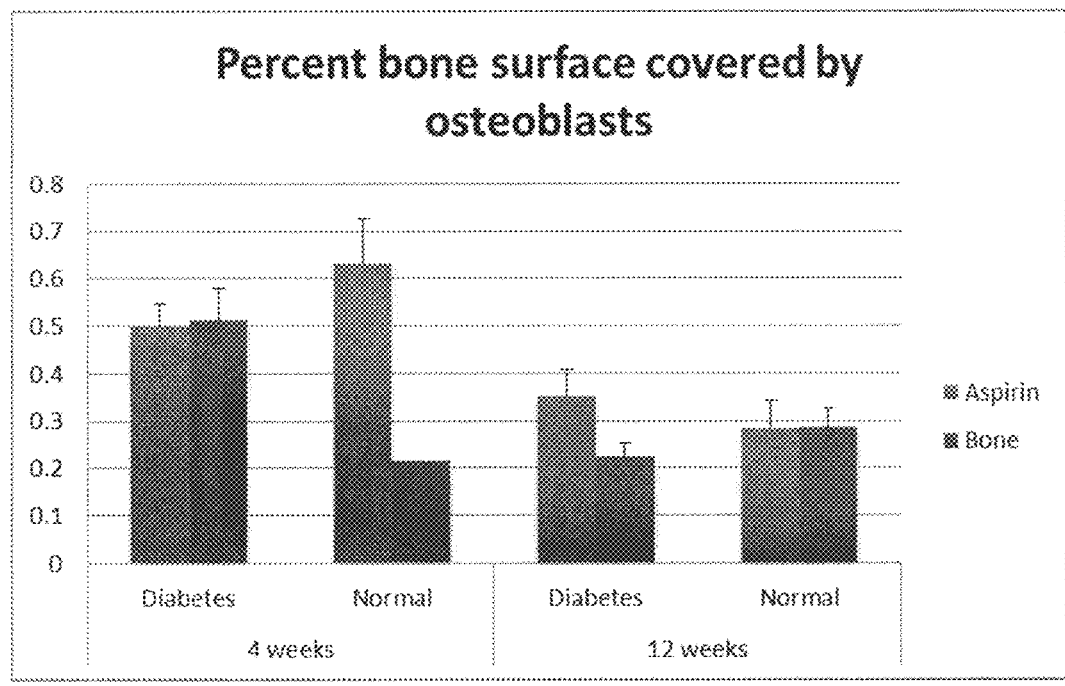
FIG. 9. Percent bone surface covered by osteoblasts, measured by dividing the length of newly formed bone surface covered by osteoblasts within the defect by the total length of newly formed bone within the defect. Bars on the left represent "aspirin" (i.e., polySAA/bone graft) and the bars on the right of each group represent "bone" (i.e., bone graft only).
Figure 10:
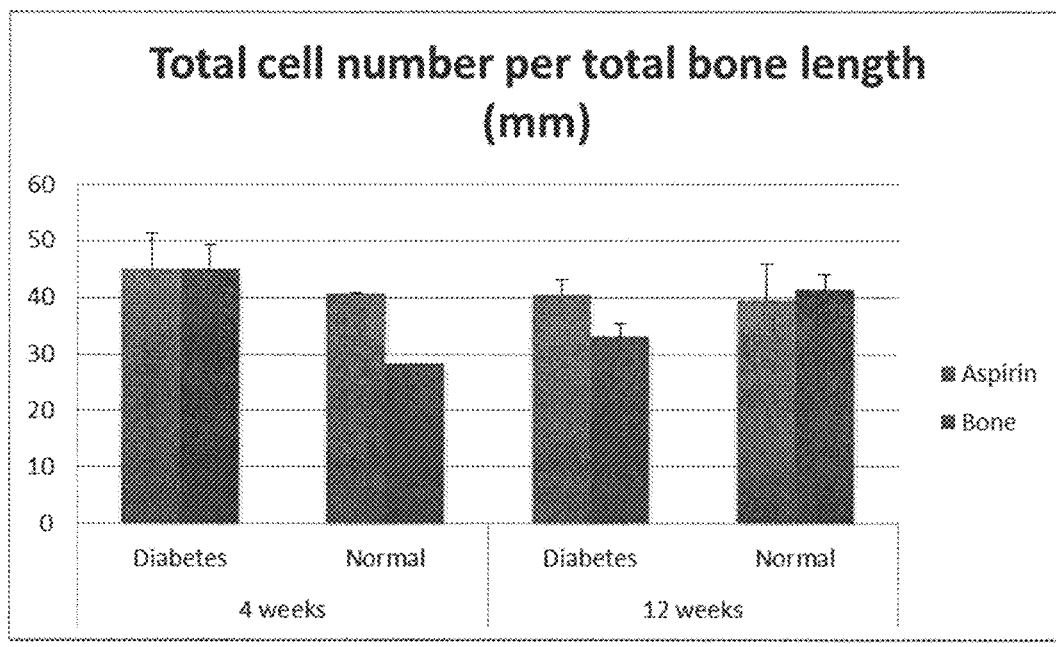
FIG. 10. Total number of cells per total bone length, measured by dividing the total number of osteoblasts and mesenchymal cells along the newly formed bone within the defect by the length of this newly formed bone. Bars on the left represent "aspirin" (i.e., polySAA/bone graft) and the bars on the right of each group represent "bone" (i.e., bone graft only).

Results from the histologic analysis at 12 weeks were similar to micro CT results at the same time point. The percent bone fill in the normoglycemic group treated with bone graft alone was increased as compared to the diabetic group treated with bone graft alone (FIG. 8). Treatment of the diabetic rats with polyaspirin resulted in increased bone fill compared to diabetic rats treated with bone graft alone ($P<0.001$) (FIG. 8). However in the normoglycemic animals the addition of polyaspirin to bone graft material did not enhance bone fill ($P>0.05$) (FIG. 8).

Discussion

The results of this study clearly demonstrate the positive effect of polyaspirin on bone regeneration in both normal and diabetic rats. Specifically, the results described herein demonstrate that polyaspirin stimulates regeneration of bone in an osseous lesion and that this is particularly prominent under conditions where bone formation is compromised such as that encountered in diabetes mellitus.

Prompt resolution of initial inflammatory process is critical for the proper wound healing and return to homeostasis. Under normal circumstances, inflammation normally resolves through an active process regulated by cellular signals. Aspirin participates in the resolution of inflammation largely through the generation of resolvins. Resolvins reduce neutrophil infiltration and expression of pro-inflammatory mediators and help stimulate clearance of apoptotic cells and stimulate removal of cellular debris. These events make it possible to jump-start resolution of acute inflammation. In this study it was found that the bone formation was accelerated by polyaspirin in normal rats at 4 weeks but not in the 12 weeks. It is possible that the accelerated bone formation can be due to the suppression of osteoclastgenesis as well as faster resolution of acute inflammation with aspirin associated resolvins.

In diabetes, resolution of inflammation is impaired in the diabetic animals. Several clinical and experimental studies have associated Type 1 diabetes mellitus with suppressed bone formation potential due to decreased osteoblastic recruitment and activity. A number of mechanisms have been proposed to explain the reduced amount of bone including the effects of diminished insulin production or insulin resistance, increased oxidative stress, increased inflammation and decreased expression of factors that promote osteoblast differentiation. These factors may affect the recruitment and survival of mesenchymal stem cells, osteoblasts numbers and production of bone. Both human and animal models establish that type 1 and type 2 diabetes reduces bone formation which delays bone accumulation during growth, and impairs fracture healing. The negative effect of diabetes on osseous healing is consistent with results that are described herein.

It is possible that the controlled release profile of polyaspirin up to 16 days was able to also modulate prolonged inflammation in diabetes effectively and consistently to resolve pro inflammatory cytokine regulation favorable for bone apposition. In other words, polyaspirin could successfully achieve faster resolution of acute inflammatory condition, deactivate the osteoclastgenesis and maintain the number of local marrow stem cells by means of suppression of apoptosis of the local bone marrow stem cells from osteotomy in the defect.

Accordingly, as described herein, treatment with polyaspirin enhances bone regeneration in diabetic rats and accelerates it in normoglycemic animals.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for decreasing bone resorption or increasing bone formation or promoting bone healing at a site in the body of a diabetic mammal in need thereof comprising, administering at or near the site a biodegradable polymer comprising repeating units of formula (Ia) in the polymer backbone:

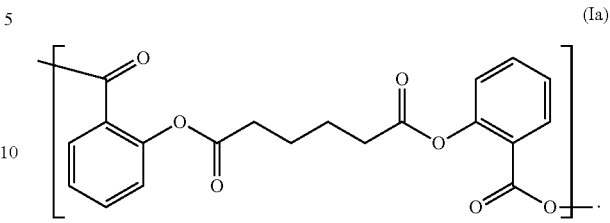

2. The method of claim 1, further comprising a second biologically active agent dispersed in a matrix of the polymer.

3. The method of claim 2, wherein the second biologically active agent is a non-steroidal anti-inflammatory, an antibacterial, an analgesic, an antioxidant or a growth factor.

4. The method of claim 1, further comprising a second biologically active agent appended to the polymer backbone.

5. The method of claim 4, wherein the second biologically active agent is a non-steroidal anti-inflammatory, an antibacterial, an analgesic, an antioxidant or a growth factor.

6. The method of claim 1, wherein a composition comprising the biodegradable polymer and a bone allograft are administered to the mammal.

7. The method of claim 6, wherein the composition further comprises mineral oil.

8. The method of claim 1, which is a method to decrease bone resorption.

9. The method of claim 1, which is a method to promote healing of bone.

10. The method of claim 1, wherein the biodegradable polymer is administered at the site of a bone fracture.

11. The method of claim 1, wherein the biodegradable polymer has an average molecular weight of about 1,500 to about 50,000 daltons.

12. The method of claim 1, further comprising administering a membrane at or near the site.

13. The method of claim 3, wherein the growth factor is a bone morphogenetic protein (BMP).

14. The method of claim 1, wherein a composition comprising the biodegradable polymer and a therapeutic agent are administered to the mammal.

15. The method of claim 14, wherein the therapeutic agent is:
    a) an anti-inflammatory agent selected from a non-steroidal anti-inflammatory and an anti-inflammatory steroid; or
    b) an agent that promotes bone healing selected from a bis-phosphonate, a hormone and a growth factor.

16. The method of claim 15, wherein the hormone is parathyroid hormone (PTH).

17. The method of claim 15, wherein the growth factor is bone morphogenetic protein (BMP).

* * * * *

UNITED STATES PATENT AND TRADEMARK OFFICE
CERTIFICATE OF CORRECTION

| | |
|---|---|
| PATENT NO. | : 9,387,250 B2 |
| APPLICATION NO. | : 14/218492 |
| DATED | : July 12, 2016 |
| INVENTOR(S) | : Kathryn E. Uhrich et al. |

It is certified that error appears in the above-identified patent and that said Letters Patent is hereby corrected as shown below:

In the Specification

Column 1, Lines 14-16, please delete "This invention was made with government support under DE13207 awarded by the National Institutes of Health. The government has certain rights in the invention." and insert -- This invention was made with government support under grant number DE013207 awarded by the National Institutes of Health. The government has certain rights in the invention. -- therefor.

Signed and Sealed this
Tenth Day of January, 2023

Katherine Kelly Vidal
*Director of the United States Patent and Trademark Office*